United States Patent
Kogiso

(10) Patent No.: US 9,820,725 B2
(45) Date of Patent: Nov. 21, 2017

(54) MUCOUS MEMBRANE LIFTING INSTRUMENT FOR ENDOSCOPE AND ENDOSCOPE TREATMENT SYSTEM

(71) Applicant: OLYMPUS CORPORATION, Hachioji-shi, Tokyo (JP)

(72) Inventor: Junichi Kogiso, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/336,356

(22) Filed: Oct. 27, 2016

(65) Prior Publication Data

US 2017/0042522 A1 Feb. 16, 2017

Related U.S. Application Data

(63) Continuation of application No. PCT/JP2015/062966, filed on Apr. 30, 2015.

(30) Foreign Application Priority Data

May 2, 2014 (JP) .................................. 2014-095477

(51) Int. Cl.
*A61B 1/00* (2006.01)
*A61B 17/00* (2006.01)
(Continued)

(52) U.S. Cl.
CPC .......... *A61B 17/00234* (2013.01); *A61B 1/00* (2013.01); *A61B 1/00087* (2013.01);
(Continued)

(58) Field of Classification Search
CPC ......... A61B 2017/00234; A61B 2017/320016; A61B 2017/0218; A61B 1/0087;
(Continued)

(56) References Cited

U.S. PATENT DOCUMENTS

| 2008/0132759 A1 | 6/2008 | Miyamoto et al. |
| 2009/0023987 A1 | 1/2009 | Okada et al. |
| 2010/0030019 A1 | 2/2010 | Kuroda et al. |

FOREIGN PATENT DOCUMENTS

| JP | 2002-045369 A | 2/2002 |
| JP | 2006-304830 A | 11/2006 |

(Continued)

OTHER PUBLICATIONS

Jul. 21, 2015 Search Report issued in International Patent Application No. PCT/JP2015/062966.

*Primary Examiner* — Timothy J Neal
(74) *Attorney, Agent, or Firm* — Oliff PLC

(57) ABSTRACT

A mucous membrane lifting instrument for an endoscope includes a first support portion which has an outer circumference surface and a longitudinal axis; a second support portion which is provided at a position spaced from the outer circumference surface of the first support portion, and has an outer circumference surface and a longitudinal axis; a pressing portion which has a proximal end and a distal end connected to the proximal end thereof and positioned more distally than the distal end portion of the endoscope; a lifting portion which is connected to the distal end of the pressing portion, extended from the distal end of the pressing portion, and passes through the space between the first support portion and the second support portion; and an attachment member configured to attach both of the first pressing portion and the second pressing portion to the endoscope.

6 Claims, 8 Drawing Sheets

(51) Int. Cl.
  *A61B 18/12*   (2006.01)
  *A61B 1/018*   (2006.01)
  *A61B 17/02*   (2006.01)
  *A61B 17/32*   (2006.01)
  *A61B 18/14*   (2006.01)
  *A61B 1/04*    (2006.01)
  *A61B 18/00*   (2006.01)

(52) U.S. Cl.
  CPC .......... *A61B 1/018* (2013.01); *A61B 17/0218* (2013.01); *A61B 17/320016* (2013.01); *A61B 18/12* (2013.01); *A61B 18/14* (2013.01); *A61B 2017/00269* (2013.01); *A61B 2017/320044* (2013.01); *A61B 2018/00482* (2013.01); *A61B 2018/00601* (2013.01); *A61B 2018/1412* (2013.01)

(58) Field of Classification Search
  CPC ..... A61B 1/018; A61B 1/00089; A61B 18/14; A61B 2018/00482; A61B 2018/1412
  See application file for complete search history.

(56) References Cited

FOREIGN PATENT DOCUMENTS

| | | |
|---|---|---|
| JP | 2009-219743 A | 10/2009 |
| JP | 2010-036024 A | 2/2010 |
| JP | 2013-017691 A | 1/2013 |
| WO | 2006/064868 A1 | 6/2006 |

MUCOUS MEMBRANE LIFTING INSTRUMENT FOR ENDOSCOPE AND ENDOSCOPE TREATMENT SYSTEM

This application is a continuation application based on a PCT International Application No. PCT/JP2015/062966, filed on Apr. 30, 2015, whose priority is claimed on Japanese Patent Application No. 2014-095477, filed on May 2, 2014. The contents of both the PCT International Application and the Japanese Patent Application are incorporated herein by reference.

BACKGROUND OF THE INVENTION

Field of the Invention

The present invention relates to a mucous membrane lifting instrument for an endoscope, and an endoscope treatment system.

Description of Related Art

In the related art, it is known that an endoscopic auxiliary tool is attached to a distal end portion of an insertion portion of an endoscope so as to improve the function of the endoscope.

For example, Japanese Unexamined Patent Application, First Publication No. 2002-45369 discloses an endoscope treatment system in which a hood for an endoscope serving as the endoscopic auxiliary tool is attached to a distal end portion of the insertion portion of the endoscope. The hood for an endoscope disclosed in Japanese Unexamined Patent Application, First Publication No. 2002-45369 includes a transparent cap portion having a substantially cylindrical shape and a substantially cylindrical endoscope-mounting portion which causes the hood for an endoscope to be fixed to the distal end portion of the insertion portion of the endoscope in an attachable/detachable manner.

An endoscope latch portion is provided in a distal end portion of the endoscope-mounting portion so as to protrude inward. A claw portion is provided in a distal end portion of the cap portion so as to protrude inward.

When the endoscope treatment system having such a configuration is used, the insertion portion of the endoscope is inserted into the endoscope-mounting portion until the distal end of the insertion portion of the endoscope reaches a position so as to abut the endoscope latch portion. The endoscope-mounting portion of the hood for an endoscope is fixed to the distal end of the insertion portion of the endoscope in a state where the distal end of the insertion portion of the endoscope does not enter the cap portion.

A distal end opening portion of the cap portion of the hood for an endoscope disclosed in Japanese Unexamined Patent Application, First Publication No. 2002-45369 is pressed to a site which is a treatment target, for example, a mucous membrane in a mucous membrane resection target site. As disclosed in Japanese Unexamined Patent Application, First Publication No. 2002-45369, when the endoscope treatment system is used, an operator of the endoscope treatment system protrudes a snare wire in a state where a distal end portion of the snare wire protruding from a snare sheath is in contact with the claw portion. As a result, the snare wire is widened on the circumference along the inner peripheral surface of the distal end portion of the cap portion and is disposed at the root of a bulged resection site in the mucous membrane. Subsequently, the operator retracts the snare wire into the snare sheath and clamps the root portion of the resection site in the mucous membrane. Thereafter, the mucous membrane can be resected by supplying a high frequency to the snare wire.

Endoscopic submucosal dissection (ESD) is known that in which a high-frequency knife is introduced into a body cavity through a channel formed in the insertion portion of the endoscope, and a lesion mucous membrane site is separated by using the high-frequency knife is known.

First, the operator performing the endoscopic submucosal dissection introduces an injection needle into a body cavity through the channel of the endoscope in an endoscopic manner. Subsequently, the operator infuses a physiological saline solution into a submucosal layer of the lesion mucous membrane site by using the injection needle to cause the lesion mucous membrane site to bulge. Moreover, the operator mounts a counter electrode plate of the high-frequency knife to a patient. Thereafter, the operator introduces the high-frequency knife having a known needle-like electrode into the body cavity in an endoscopic manner. The operator supplies power to the electrode and punctures a site around the lesion mucous membrane site with the electrode. When the electrode is moved in a transverse direction along the site around the lesion mucous membrane site, the submucosal layer around the lesion mucous membrane site is incised.

SUMMARY OF THE INVENTION

According to a first aspect of the present invention, a mucous membrane lifting instrument for an endoscope includes a first support portion which has an outer circumference surface and a longitudinal axis extending distally from a distal end portion of an endoscope; a second support portion which is provided at a position spaced from the outer circumference surface of the first support portion, and has an outer circumference surface and a longitudinal axis extending distally from the distal end portion of the endoscope; a pressing portion which has a proximal end supported by the distal end portion of the endoscope, and has a distal end connected to the proximal end thereof and positioned more distally than the distal end portion of the endoscope, wherein the pressing portion includes: a first pressing portion which has an outer circumference surface and is extended distally from the distal end portion of the endoscope, and a second pressing portion which is disposed at a position spaced from the outer circumference surface of the first pressing portion, has an outer circumference surface, and is extended distally from the distal end portion of the endoscope; a lifting portion which is connected to the distal end of the pressing portion, extended from the distal end of the pressing portion towards a space between the first support portion and the second support portion, and passes through the space between the first support portion and the second support portion while having a gap with respect to each of the first support portion and the second support portion; and an attachment member configured to attach both of the first pressing portion and the second pressing portion to the endoscope, wherein the lifting portion includes: a first lifting portion which has an outer circumference surface and is connected to a distal end of the first pressing portion, and a second lifting portion which is disposed at a position spaced from the outer circumference surface of the first lifting portion, has an outer circumference surface, and is connected to a distal end portion of the second pressing portion.

According to a second aspect of the present invention, in the mucous membrane lifting instrument for an endoscope according to the first aspect, the first support portion may be formed to extend from the distal end portion of the endoscope while being inclined with respect to the first lifting portion, and the second support portion may be formed to extend from the distal end portion of the endoscope while being inclined with respect to the first lifting portion.

According to a third aspect of the present invention, the mucous membrane lifting instrument for an endoscope according to the first aspect may further include a connecting portion which is provided to connect a proximal end of the first lifting portion and a proximal end of the second lifting portion.

According to a fourth aspect of the present invention, in the mucous membrane lifting instrument for an endoscope according to the first aspect, each of the first lifting portion, the second lifting portion, the first support portion, and the second support portion may have a rod shape.

According to a fifth aspect of the present invention, the mucous membrane lifting instrument for an endoscope according to the first aspect may further include a connecting portion which is provided to connect a distal end of the first support portion and a distal end of the second support portion.

According to a sixth aspect of the present invention, an endoscope treatment system includes the mucous membrane lifting instrument for an endoscope according to claim 1; and an endoscope to which the mucous membrane lifting instrument for an endoscope is attached.

DETAILED DESCRIPTION OF THE INVENTION

Figure 1:
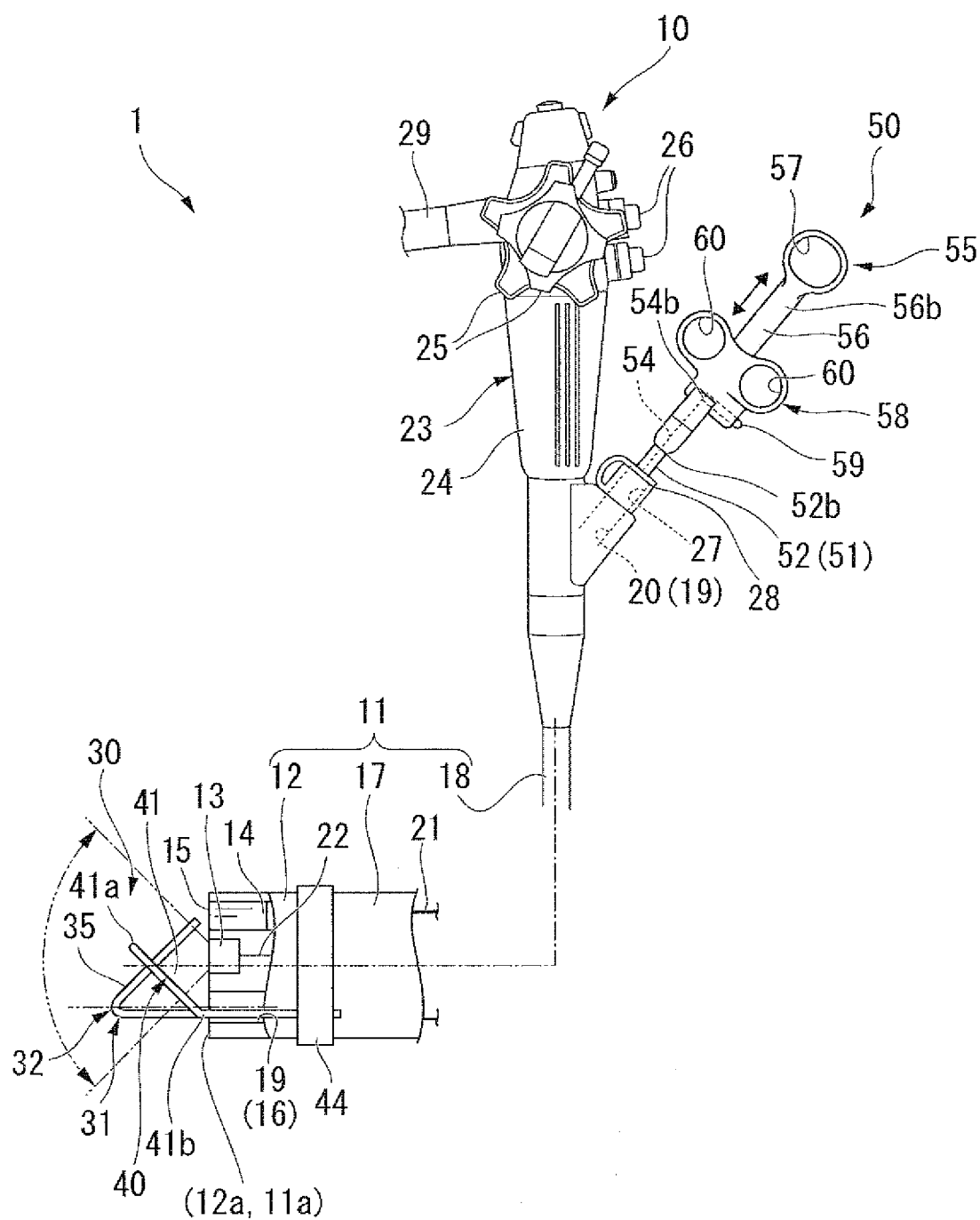
FIG. 1 is a general view showing an endoscope treatment system according to an embodiment of the present invention.
Figure 2:
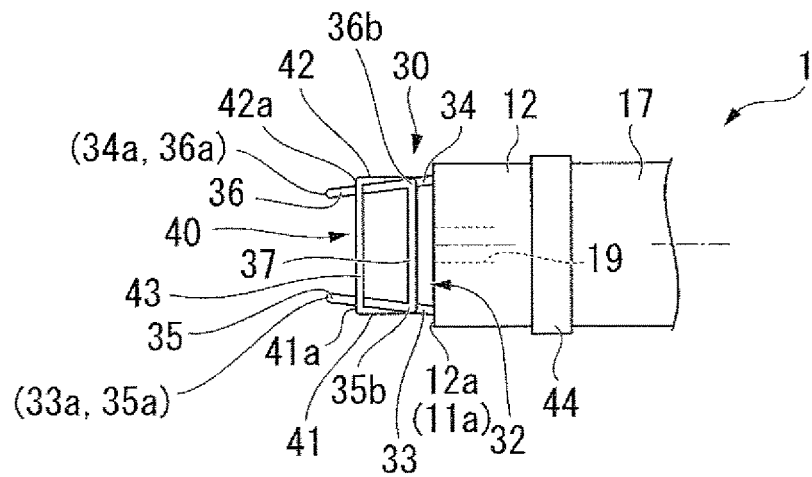
FIG. 2 is a plan view showing a configuration of a distal portion of the endoscope treatment system according to the embodiment of the present invention.
Figure 3:
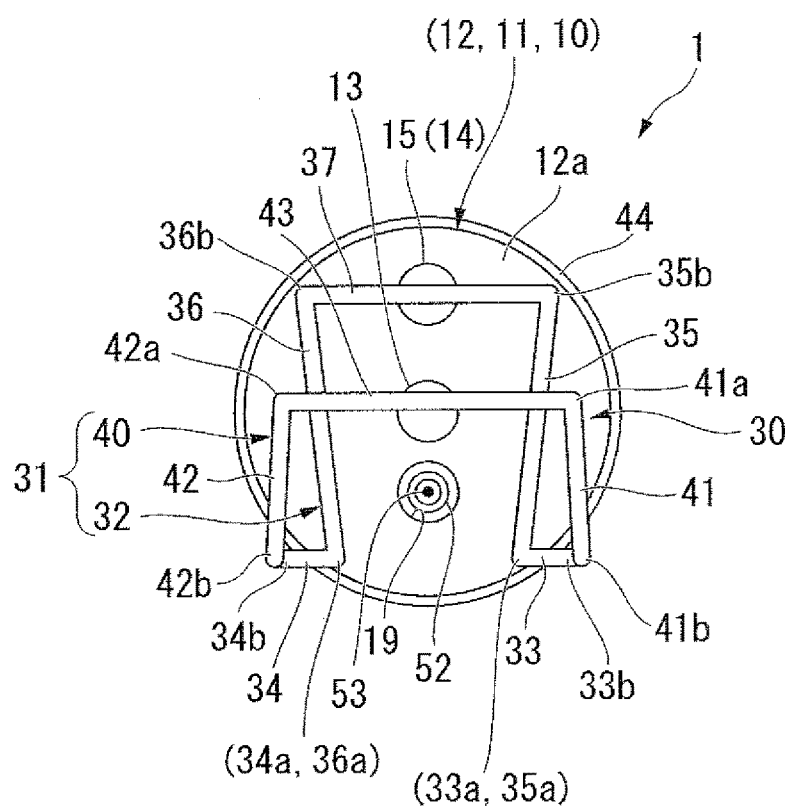
FIG. 3 is a front view showing a mucous membrane lifting instrument for an endoscope, and an endoscope in the endoscope treatment system according to the embodiment of the present invention.

Hereinafter, an embodiment of the present invention will be described. FIG. 1 is a general view showing an endoscope treatment system (ESD treatment system 1) according to the present embodiment. FIG. 2 is a plan view showing a configuration of a distal portion of the ESD treatment system 1. FIG. 3 is a front view showing a mucous membrane lifting instrument 30 for an endoscope, and an endoscope 10 in the ESD treatment system 1.

The ESD treatment system 1 of the present embodiment shown in FIG. 1 is an endoscope treatment system having a configuration suitable for performing endoscopic submucosal dissection (ESD).

As shown in FIG. 1, the ESD treatment system 1 includes the endoscope 10, the mucous membrane lifting instrument 30 for an endoscope, and a incision instrument 50 for an endoscope.

The endoscope 10 includes an insertion portion 11, an operation unit 23, and a universal cable 29.

The insertion portion 11 is an elongated member which can be inserted into a human body.

The insertion portion 11 includes a rigid distal portion 12, a bending portion 17, and a flexible tube portion 18.

The rigid distal portion 12 is disposed on the outermost distal side of the insertion portion 11.

The rigid distal portion 12 has an observation unit 13 for observing a treatment target site, an illumination portion 14 which irradiates the treatment target site with illumination light, and a distal opening portion 16 of a treatment tool channel 19. The distal opening portion 16 of the treatment tool channel 19 serves as a passage through which a treatment tool for an endoscope such as the incision instrument 50 for an endoscope protrudes forward.

For example, the observation unit 13 includes a solid-state image capturing device such as a charge coupled device (CCD) area image sensor, and an optical system (none thereof shown). In the present embodiment, the observation unit 13 has a so-called direct-viewing-type configuration in which a visual field of image capturing is set in the forward direction of the insertion portion 11. The configuration of the observation unit 13 is not particularly limited. Any type of configuration may be applied as long as image-capturing means which can be applied to a known endoscope is appropriately selected and applied as an image-capturing unit.

The illumination portion 14 includes a light source (not shown) such as a light-emitting diode (LED), a laser diode (LD), and an incandescent light bulb, and a light-emitting portion 15 which radiates light emitted from the light source, in the forward direction of the insertion portion 11 as illumination light. The configuration of the illumination portion 14 is not particularly limited. In place of the configuration in which the light source is disposed in the rigid distal portion 12 and emits illumination light, illumination light may be optically guided through an optical fiber from an external light source connected through the universal cable 29.

The distal opening portion 16 of the treatment tool channel 19 is open on a distal end surface 12a of the rigid distal portion 12. The treatment tool channel 19 is connected to the operation unit 23 through the inside of the rigid distal portion 12, the inside of the bending portion 17, and the inside of the flexible tube portion 18. The treatment tool channel 19 has a proximal opening portion 27 inside the operation unit 23. In the present embodiment, the treatment tool for an endoscope such as the incision instrument 50 for an endoscope can be inserted into the proximal opening portion 27 of the treatment tool channel 19 via a forceps plug 28 which will be described later.

The bending portion 17 can be bent in response to an operation of an angle knob 25 disposed in the operation unit 23.

The flexible tube portion 18 is a tubular member formed by a resin or the like. Inside the flexible tube portion 18, a channel tube 20, an angle wire 21, and wiring 22 are disposed. The channel tube 20 is configured to form the treatment tool channel 19. The angle wire 21 is provided so as to transmit power from the operation unit 23 to make the bending portion 17 to be bent. The wiring 22 is provided so as to transmit electric power and signals to the observation unit 13 and the illumination portion 14.

The operation unit 23 includes a main body portion 24 which an operator grasps, the angle knob 25 for causing the bending portion 17 to be bent, switches 26 for performing various types of operations to the endoscope 10, and the forceps plug 28 communicating with the proximal opening portion 27 of the treatment tool channel 19.

Next, the configuration of the mucous membrane lifting instrument 30 for an endoscope according to the present embodiment will be described.

As shown in FIGS. 1, 2, and 3, the mucous membrane lifting instrument 30 for an endoscope is attachable and detachable with respect to an outer peripheral surface of a distal end 11a of the insertion portion 11 of the endoscope 10 according to the present embodiment. The mucous membrane lifting instrument 30 for an endoscope can be utilized by being attached to the endoscope 10 so as to lift a mucous membrane through the ESD operation.

The mucous membrane lifting instrument 30 for an endoscope includes a lifting instrument main body 31 and an attachment member 44.

The lifting instrument main body 31 is a member generating a wide working space between a submucosal layer and a muscle layer by lifting a mucous membrane spaced from the muscle layer and causing the mucous membrane to be tensioned thereafter.

The lifting instrument main body 31 includes a lifting member 32 and a push-down member 40.

In the mucous membrane lifting instrument 30 for an endoscope according to the present embodiment, the lifting member 32 is used for lifting a mucous membrane. The lifting member 32 includes a first pressing portion 33, a second pressing portion 34, a first lifting portion 35, a second lifting portion 36, and a connecting portion 37. The connecting portion 37 connects the first lifting portion 35 and the second lifting portion 36.

The first pressing portion 33 is a rod-shaped portion extending toward the distal end side in a substantially linear manner from the distal end surface 12a of the rigid distal portion 12 of the insertion portion 11.

The second pressing portion 34 is a rod-shaped portion extending toward the distal end side from the distal end surface 12a of the rigid distal portion 12 of the insertion portion 11 in a substantially linear manner. In the present embodiment, a center line of the first pressing portion 33 and a center line of the second pressing portion 34 are present on the same plane. Moreover, in the present embodiment, the first pressing portion 33 and the second pressing portion 34 are disposed such that the distance between the first pressing portion 33 and the second pressing portion 34 becomes gradually shorter toward each of the distal ends 33a and 34a. The disposition relationship between the first pressing portion 33 and the second pressing portion 34 is not limited thereto. For example, the disposition relationship therebetween is acceptable as long as the extending direction of the center line of the second pressing portion 34 is substantially parallel to the extending direction of the center line of the first pressing portion 33. In addition, without being limited to a rod shape, a shape is acceptable as long as each of the first pressing portion 33 and the second pressing portion 34 has a shape likely to be in contact with tissue. For example, a flat plate-shape may be adopted.

The first pressing portion 33 and the second pressing portion 34 are attached to the outer surface of the rigid distal portion 12 of the insertion portion 11. In the present embodiment, the first pressing portion 33 and the second pressing portion 34 are detachably attached to the rigid distal portion 12 through the attachment member 44.

The first lifting portion 35 is a rod-shaped portion connected to the distal end 33a of the first pressing portion 33 in a state of forming an angle with respect to the first pressing portion 33. In the present embodiment, the angle formed between the first lifting portion 35 and the first pressing portion 33 is set to 45°. However, the angle formed between the first lifting portion 35 and the first pressing portion 33 is not limited to 45°, and it is acceptable that the first lifting portion 35 and the first pressing portion 33 extend in directions intersecting each other. When the first lifting portion 35 and the first pressing portion 33 are caused to slip into a place underneath a mucous membrane, the mucous membrane is supported by the first lifting portion 35, and the first pressing portion 33 is operated so as to press the muscle layer side to maintain a space for performing treatment underneath the mucous membrane.

The second lifting portion 36 is a rod-shaped portion connected to the distal end 34a of the second pressing portion 34 in a state of forming an angle with respect to the second pressing portion 34. In the present embodiment, the angle formed between the second lifting portion 36 and the second pressing portion 34 is set to 45°. However, the angle formed between the second lifting portion 36 and the second pressing portion 34 is not limited to 45°, and it is acceptable that the second lifting portion 36 and the second pressing portion 34 extend in directions intersecting each other. When the second lifting portion 36 and the second pressing portion 34 are caused to slip into a place underneath a mucous membrane together with the first lifting portion 35 and the first pressing portion 33, the mucous membrane is supported by the second lifting portion 36, and the second pressing portion 34 is operated so as to press the muscle layer side to maintain a space for performing treatment underneath the mucous membrane.

Both a distal end 35a of the first lifting portion 35 and a distal end 36a of the second lifting portion 36 are disposed on a distal side from the distal end surface 12a of the insertion portion 11. In addition, the distal end 35a of the first lifting portion 35 and the distal end 36a of the second lifting portion 36 have a positional relationship such that the axial line of the below-described treatment tool channel 19 is interposed therebetween in the orthogonal direction orthogonal to the axial line of the insertion portion 11.

The connecting portion 37 connecting the first lifting portion 35 and the second lifting portion 36 is a rod-shaped portion and provided to connect a proximal end 35b of the first lifting portion 35 and a proximal end 36b of the second lifting portion 36. Even if no connecting portion 37 is provided, the first lifting portion 35 and the second lifting portion 36 can exhibit similar effects, however, it is preferable to provide the connecting portion 37.

In the present embodiment, for example, each of the first pressing portion 33, the second pressing portion 34, the first lifting portion 35, the second lifting portion 36, and the connecting portion 37 has a metal rod-shaped member, has insulation coating covering the outer surface of the rod-shaped member, and is formed by bending the rod-shaped member.

The push-down member 40 includes a first support portion 41, a second support portion 42, and a connecting portion 43. The connecting portion 43 is provided to connect the first support portion 41 and the second support portion 42.

The first support portion 41 is provided while being spaced from the outer circumference surface of the first lifting portion 35 to the outside with a gap therebetween.

In the present embodiment, the first support portion 41 is a rod-shaped portion which forms an angle with respect to the first pressing portion 33 and is fixed to a position in the vicinity of a proximal end 33b of the first pressing portion 33. A portion fixed to the first pressing portion 33 in the first support portion 41, for example, is a proximal end 41b of the first support portion 41. It is acceptable that the extending direction of the first support portion 41 forms an angle with respect to the central axis of the first lifting portion 35, and it is not necessary that the extending direction forms an angle with respect to the first pressing portion 33.

The second support portion 42 is provided at a position facing the first support portion 41 with respect to the first lifting portion 35 and the second lifting portion 36 while being spaced from the outer circumference surface of the second lifting portion 36 to the outside with a gap therebetween.

The second support portion 42 is a rod-shaped portion which forms an angle with respect to the second pressing portion 34 and is fixed to a position in the vicinity of a proximal end 34b of the second pressing portion 34. A portion fixed to the second pressing portion 34 in the second support portion 42, for example, is a proximal end 42b of the second support portion 42. It is acceptable that the extending direction of the second support portion 42 forms an angle with respect to the central axis of the second lifting portion 36 and it is not necessary that the extending direction forms an angle with respect to the second pressing portion 34.

When the mucous membrane lifting instrument 30 for an endoscope is viewed in a direction in which the first lifting portion 35 and the second lifting portion 36 overlap each other, the central axis of the first support portion 41 extends in a direction intersecting the central axis of the first lifting portion 35, and the central axis of the second support portion 42 extends in a direction intersecting the central axis of the second lifting portion 36. More preferably, when the mucous membrane lifting instrument 30 for an endoscope is viewed in a direction in which the first lifting portion 35 and the second lifting portion 36 overlap each other, the central axis of the first support portion 41 intersects the central axis of the first lifting portion 35, and the central axis of the second support portion 42 intersects the central axis of the second lifting portion 36.

The connecting portion 43 connecting the first support portion 41 and the second support portion 42 is a rod-shaped portion provided to connect a distal end 41a of the first support portion 41 and a distal end 42a of the second support portion 42 to be connected with each other.

For example, the attachment member 44 is a resin band and can hold the first pressing portion 33 and the second pressing portion 34 in a state where the first pressing portion 33 and the second pressing portion 34 are in contact with the outer surface of the rigid distal portion 12 of the insertion portion 11 of the endoscope 10. The attachment member 44 can be detached from the rigid distal portion 12 of the insertion portion 11 through manual work or the like of an operator.

Next, the configuration of the incision instrument 50 for an endoscope attached to the endoscope 10 according to the present embodiment will be described.

The incision instrument 50 for an endoscope shown in FIG. 1 is a treatment tool for incising biological tissue. A known incision instrument for an endoscope may be appropriately selected and applied as the incision instrument 50 for an endoscope according to the present embodiment. For example, as the incision instrument 50 for an endoscope, a high-frequency knife which incises biological tissue through cauterization performed by a high-frequency current supplied from a high-frequency power source apparatus is applied.

The incision instrument 50 (high-frequency knife 50) for an endoscope according to the present embodiment includes a treatment tool insertion portion 51, a treatment tool operation unit 55, and a counter electrode plate (not shown).

The treatment tool insertion portion 51 includes a sheath 52, an incising electrode 53, and a power supply wire 54.

The sheath 52 is a tubular member having flexibility and has insulation properties. The power supply wire 54 is disposed inside the sheath 52 and is capable of advancing and retracting.

Figure 4:
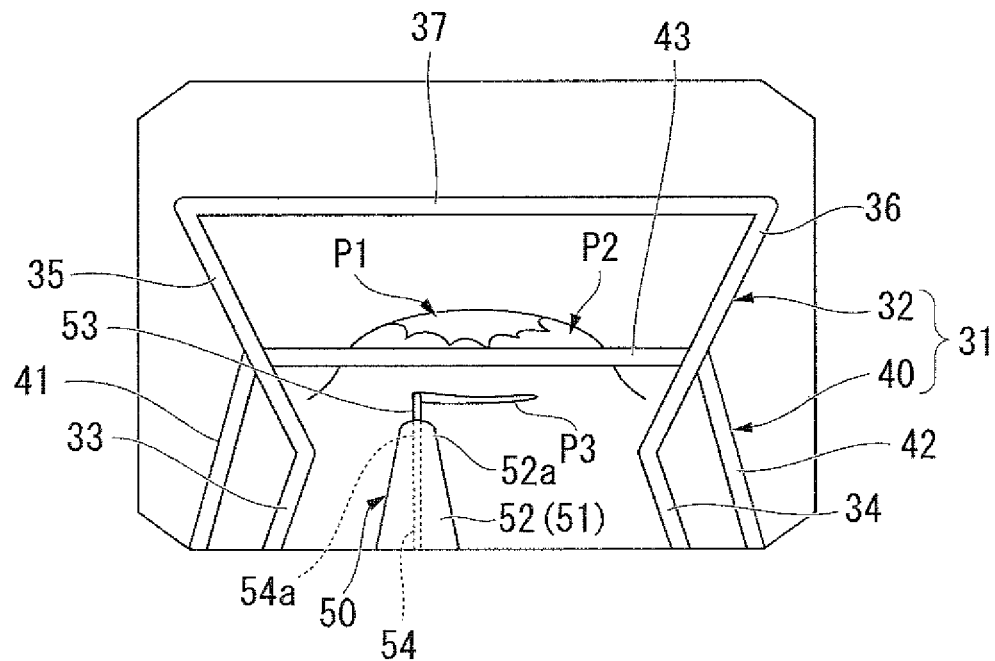
FIG. 4 is a view showing an example of an endoscopic image captured when the endoscope treatment system according to the embodiment of the present invention is used.

The incising electrode 53 shown in FIGS. 3 and 4 is an electrode fixed to a distal end 54a of the power supply wire 54. Cauterization or incision of biological tissue is performed by bringing the incising electrode 53 into contact with the biological tissue in a state where a high-frequency current is supplied thereto.

Figure 6:
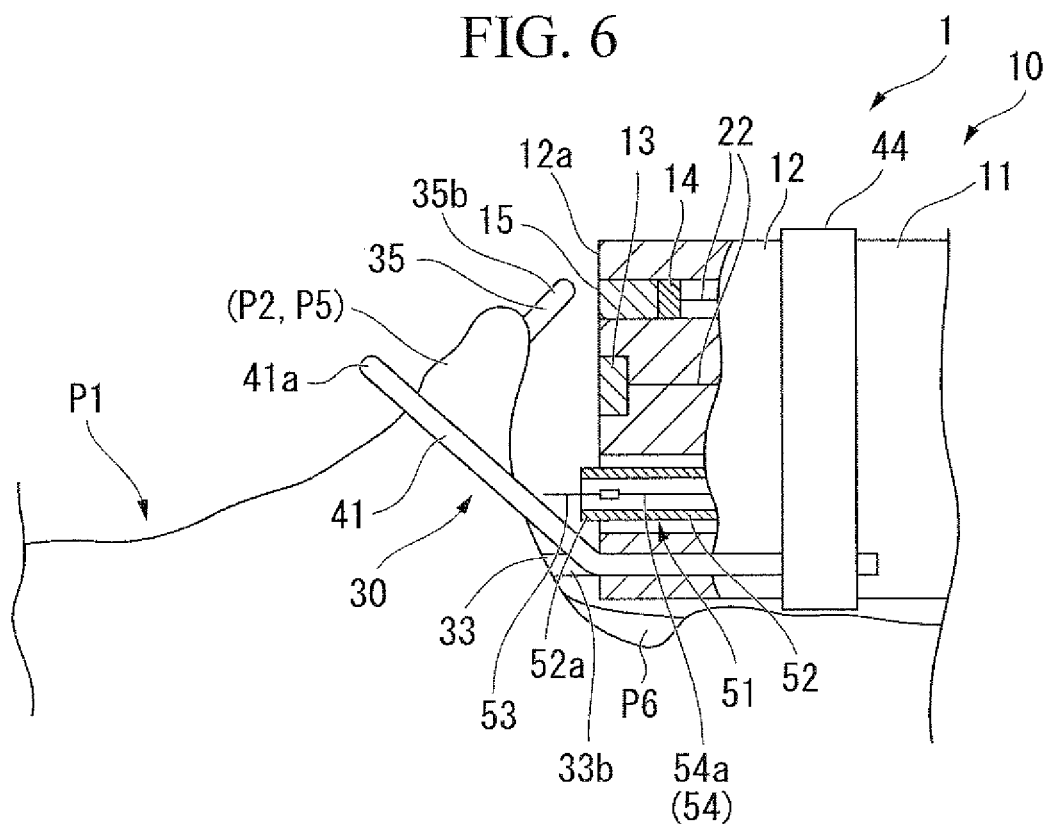
FIG. 6 is a side view showing a state where the mucous membrane lifting instrument for an endoscope in the endoscope treatment system according to the embodiment of the present invention lifts a mucous membrane.

As shown in FIG. 1, when the power supply wire 54 is moved to a proximal end 52b side of the sheath 52, the incising electrode 53 is completely accommodated inside the sheath 52 through an opening of a distal end 52a of the sheath 52 (refer to FIG. 6). When the power supply wire 54 is moved to the distal end 52a side of the sheath 52, the incising electrode 53 protrudes from the opening of the distal end 52a of the sheath 52.

The power supply wire 54 shown in FIG. 1 is a conductive member for supplying a high-frequency current to the incising electrode 53. The distal end 54a of the power supply wire 54 (refer to FIG. 6) is fixed to the incising electrode 53. A proximal end 54b of the power supply wire 54 (refer to FIG. 1) is disposed in the treatment tool operation unit 55. The proximal end 54b of the power supply wire 54 is fixed to a slider 58 (will be described later). The power supply wire 54 advances/retracts inside the sheath 52 in response to an operation of the slider 58.

As shown in FIG. 1, the treatment tool operation unit 55 includes a rod-shaped operation unit main body 56 and the slider 58. The operation unit main body 56 is fixed to the proximal end 52b of the sheath 52. The slider 58 is provided so as to be slidable relative to the operation unit main body 56 in the longitudinal direction of the operation unit main body 56.

A proximal end 56b of the operation unit main body 56 includes a finger-hooking ring 57.

The slider 58 is connected with the operation unit main body 56 so as to be capable of advancing and retracting in the longitudinal direction of the operation unit main body 56. The slider 58 includes a connector 59 fixed to the proximal end 54b of the power supply wire 54, and a finger-hooking ring 60.

The connector 59 provided in the slider 58 can be connected to the high-frequency power source apparatus (not shown). A high-frequency current output from the high-frequency power source apparatus is transmitted from the high-frequency power source apparatus to the incising electrode 53 through the connector 59 and the power supply wire 54.

When an operator hooks fingers into the ring 57 provided in the operation unit main body 56 and the ring 60 provided in the slider 58 and conducts opening-closing motion of the hand, the slider 58 can advance and retract relative to the operation unit main body 56.

Next, the operation of the ESD treatment system 1 of the present embodiment will be described.

Hereinafter, operation during mucous membrane resection performed inside a body cavity by using the ESD treatment system 1 of the present embodiment will be described as an example.

Figure 5:
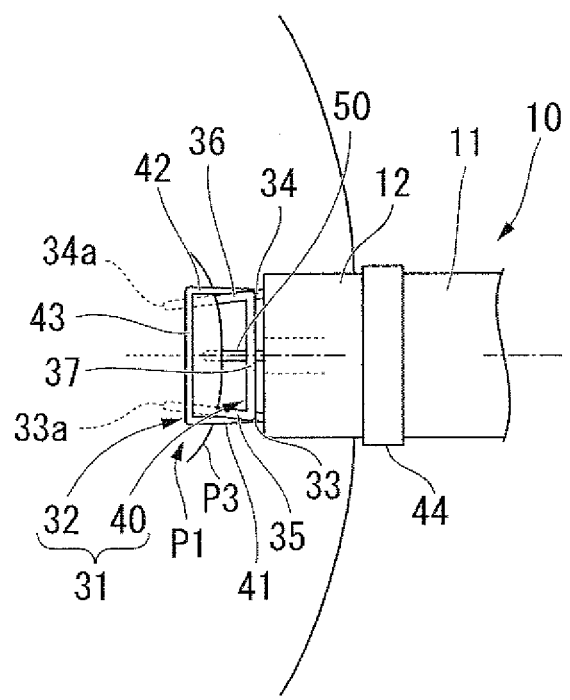
FIG. 5 is a view showing a process performed when the endoscope treatment system according to the embodiment of the present invention is used.
Figure 7:
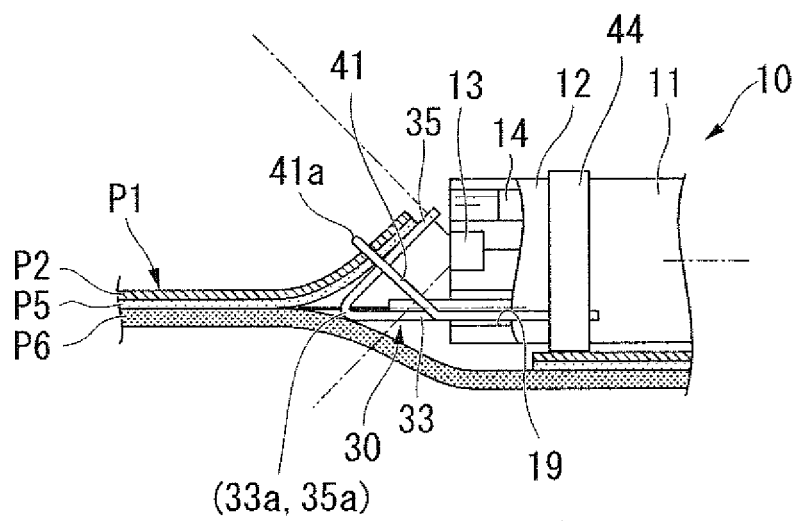
FIG. 7 is a sectional view which is viewed from the side and partially shows a state where the mucous membrane lifting instrument for an endoscope in the endoscope treatment system according to the embodiment of the present invention lifts a mucous membrane.
Figure 8:
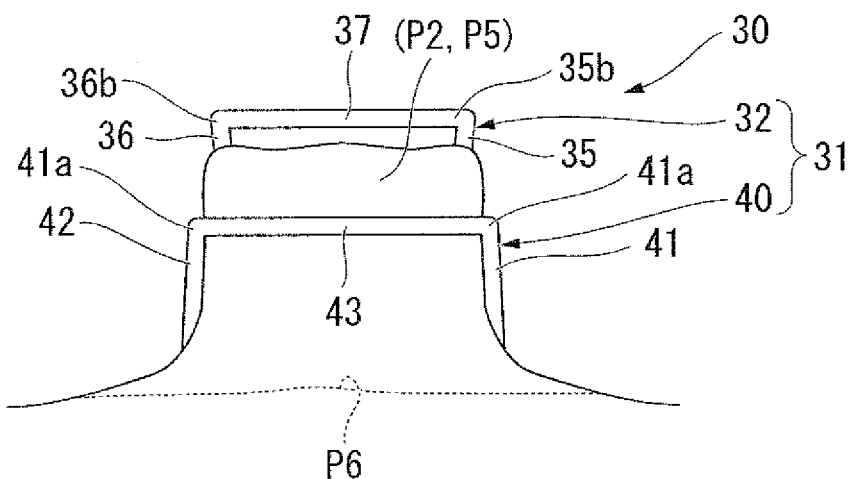
FIG. 8 is a front view showing a state where the mucous membrane lifting instrument for an endoscope in the endoscope treatment system according to the embodiment of the present invention lifts a mucous membrane.
Figure 9:
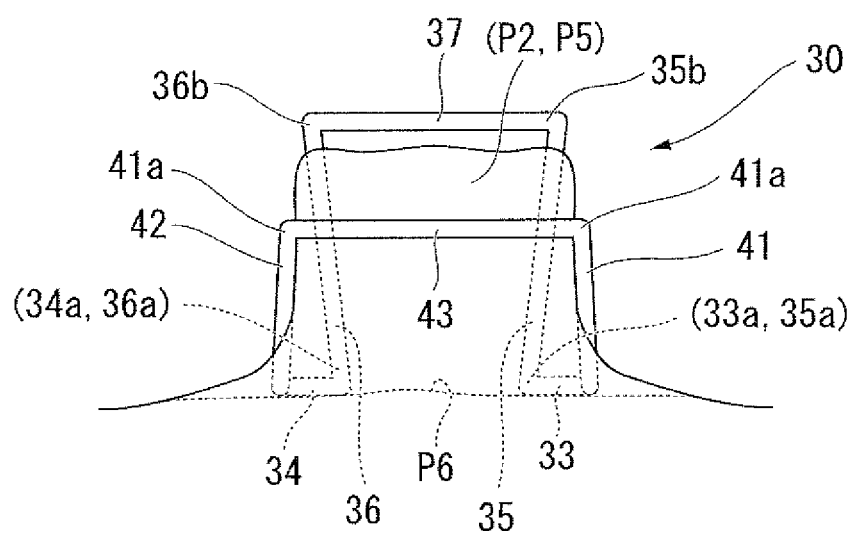
FIG. 9 is another front view showing a state where the mucous membrane lifting instrument for an endoscope in the endoscope treatment system according to the embodiment of the present invention lifts a mucous membrane.
Figure 10:
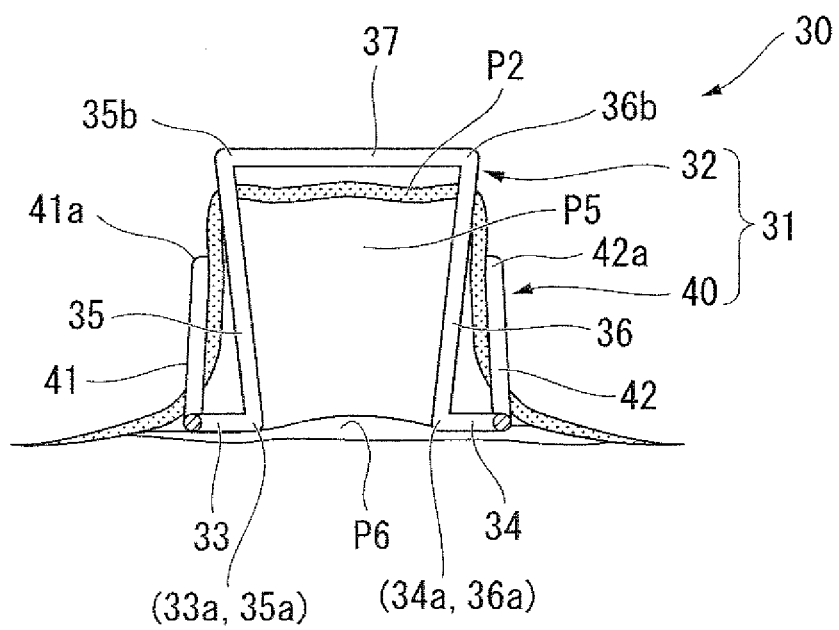
FIG. 10 is a rear view showing a state where the mucous membrane lifting instrument for an endoscope in the endoscope treatment system according to the embodiment of the present invention lifts a mucous membrane, and the view shows a lifting state of the mucous membrane when viewed in a visual direction of an endoscopic image captured by the endoscope.

FIG. 4 is a view showing an example of an endoscopic image captured when the ESD treatment system 1 is used. FIG. 5 is a view showing a process performed when the ESD treatment system 1 is used. FIG. 6 is a side view showing a state where the mucous membrane lifting instrument 30 for an endoscope lifts a mucous membrane. FIG. 7 is a sectional view which is viewed from the side and partially shows a state where the mucous membrane lifting instrument 30 for an endoscope lifts a mucous membrane. FIG. 8 is a front view showing a state where the mucous membrane lifting instrument 30 for an endoscope lifts a mucous membrane. FIG. 9 is another front view showing a state where the mucous membrane lifting instrument 30 for an endoscope lifts the mucous membrane. FIG. 10 is a rear view showing a state where the mucous membrane lifting instrument 30 for an endoscope lifts a mucous membrane, and the view shows a lifting state of the mucous membrane when viewed in a visual direction of an endoscopic image captured by the endoscope 10.

Before the ESD treatment system 1 shown in FIG. 1 is used, the counter electrode plate of the high-frequency knife 50 is mounted on a patient. Before the ESD treatment system 1 is used, the mucous membrane lifting instrument 30 for an endoscope according to the present embodiment is attached to the rigid distal portion 12 of the insertion portion 11 through the attachment member 44.

An operator of the ESD treatment system 1 performs a known operation, for example, in which the distal end 11a of the insertion portion 11 of the endoscope 10 is introduced into the gastrointestinal tract from the mouth, and the distal end 11a of the insertion portion 11 is guided to the treatment target site. In this case, as necessary, the position of the distal end 11a of the insertion portion 11 is adjusted while bending the bending portion 17 by operating the angle knob 25 such that a lesion mucous membrane site P1 (refer to FIG. 4) which is a resection target site is secured in the visual field of the endoscope 10.

In a state where the operator holds the position of the distal end 11a of the insertion portion 11 with respect to the patient, the operator introduces an injection needle (not shown) into the gastrointestinal tract through the forceps plug 28 and the treatment tool channel 19 of the endoscope 10. The operator uses the injection needle introduced into the gastrointestinal tract and infuses a physiological saline solution into a submucosal layer of the lesion mucous membrane site P1, thereby causing the lesion mucous membrane site P1 to bulge. When the lesion mucous membrane site P1 bulges, the operator pulls the injection needle out of the treatment tool channel 19.

Next, as shown in FIG. 1, the operator inserts the high-frequency knife 50 into the treatment tool channel 19. The high-frequency knife 50 is prepared in a state where the incising electrode 53 is accommodated inside the sheath 52. The high-frequency knife 50 is prepared in a state where the connector 59 of the high-frequency knife 50 is connected to the high-frequency power source apparatus.

The operator introduces the treatment tool insertion portion 51 of the high-frequency knife 50 into the treatment tool channel 19 through the forceps plug 28 shown in FIG. 1. The operator stops the treatment tool insertion portion 51 when the treatment tool insertion portion 51 protrudes from the distal end 11a of the insertion portion 11.

As shown in FIG. 4, a state of the distal end 52a of the sheath 52 disposed between the first pressing portion 33 and the second pressing portion 34 can be visually recognized from an endoscopic image acquired by using the observation unit 13 of the endoscope 10.

The operator moves the slider 58 of the treatment tool operation unit 55 shown in FIG. 1 relative to the operation unit main body 56 and causes the incising electrode 53 to protrude from the sheath 52 of the high-frequency knife 50. As necessary, the operator moves the rigid distal portion 12 of the endoscope 10 by causing the bending portion 17 of the endoscope 10 to be bent and performs positional adjustment such that the position of the incising electrode 53 reaches the scheduled resection position. Subsequently, the operator operates a switch (not shown) so as to cause the high-frequency power source apparatus to generate a high-frequency current, and the high-frequency current is supplied to the incising electrode 53 through the connector 59 and the power supply wire 54. Moreover, the operator brings the incising electrode 53 in a state where the high-frequency current is supplied into contact with tissue in the scheduled resection position, thereby incising the tissue along a predetermined scheduled incision line.

Accordingly, as shown in FIG. 4, an opening P3 is formed in a mucous membrane layer P2 of the lesion mucous membrane site P1. As shown in FIG. 5, it is acceptable that the size of the opening P3 is larger than the distance between the distal end 33a of the first pressing portion 33 and the distal end 34a of the second pressing portion 34.

After the opening P3 is formed, the operator causes the incising electrode 53 to be accommodated inside the sheath 52 and retracts the sheath 52 into the treatment tool channel 19.

Subsequently, as shown in FIGS. 5 and 6, the operator moves the insertion portion 11 of the endoscope 10 such that both the distal end 33a of the first pressing portion 33 and the distal end 34a of the second pressing portion 34 are inserted into the opening P3 formed in the mucous membrane lesion site P1.

Accordingly, the first pressing portion 33 and the second pressing portion 34 are introduced into a space between a submucosal layer P5 and a muscle layer P6. In this case, as shown in FIG. 7, the first pressing portion 33 and the second pressing portion 34 are in contact with the muscle layer P6, and the first lifting portion 35 and the second lifting portion 36 are in contact with the submucosal layer P5. Since the muscle layer P6 is held by the first pressing portion 33 and the second pressing portion 34, an operative site becomes nearly flat. The first lifting portion 35 and the second lifting portion 36 hold the submucosal layer P5 in a state of pushing up the submucosal layer P5 such that the submucosal layer P5 is spaced from the muscle layer P6.

As shown in FIGS. 8, 9, and 10, when the first pressing portion 33 and the second pressing portion 34 are further inserted through the opening P3, the submucosal layer P5 enters a space between the first lifting portion 35 and the first support portion 41, and a space between the second lifting portion 36 and the second support portion 42. Moreover, the submucosal layer P5 is pressed toward the muscle layer P6 side by the first support portion 41 and the second support portion 42.

When the submucosal layer P5 has entered the space between the first lifting portion 35 and the first support portion 41, the outer surface of the first lifting portion 35 serves as a push-up surface pushing up the submucosal layer P5. In addition, when the submucosal layer P5 has entered the space between the first lifting portion 35 and the first support portion 41, the outer surface of the first support portion 41 serves as a push-down surface pushing down the submucosal layer P5.

When the submucosal layer P5 has entered the space between the second lifting portion 36 and the second support portion 42, the outer surface of the second lifting portion 36 serves as the push-up surface pushing up the submucosal layer P5. In addition, when the submucosal layer P5 has entered the space between the second lifting portion 36 and the second support portion 42, the outer surface of the second support portion 42 serves as the push-down surface pushing down the submucosal layer P5.

Since the first lifting portion 35 and the second lifting portion 36 push up the submucosal layer P5 in a direction spaced from the muscle layer P6 and the first support portion 41 and the second support portion 42 press the submucosal layer P5 toward the muscle layer P6 side at the same time, the submucosal layer P5 receives stretching force between the first lifting portion 35 and the second lifting portion 36. Accordingly, the submucosal layer P5 between the first lifting portion 35 and the second lifting portion 36 are tensioned between the first lifting portion 35 and the second lifting portion 36 against gravity or the like drooping toward the muscle layer P6 side. Since the submucosal layer P5 is tensioned between the first lifting portion 35 and the second lifting portion 36, an operative site (working space) greater than that in a case where the submucosal layer P5 is not tensioned is generated between the submucosal layer P5 and the muscle layer P6.

In addition, since the submucosal layer P5 is tensioned between the first lifting portion 35 and the second lifting portion 36, the space between the submucosal layer P5 and the muscle layer P6 can be easily observed by using the observation unit 13.

In a state where the lifting member 32 sufficiently lifts the submucosal layer P5, the operator causes the high-frequency knife 50 shown in FIG. 1 to protrude again from the treatment tool channel 19 as shown in FIG. 6, and causes the incising electrode 53 to protrude from the sheath 52. Thereafter, the operator causes a high-frequency current to be supplied to the incising electrode 53 thereby resecting the lesion mucous membrane site P1.

Figure 13:
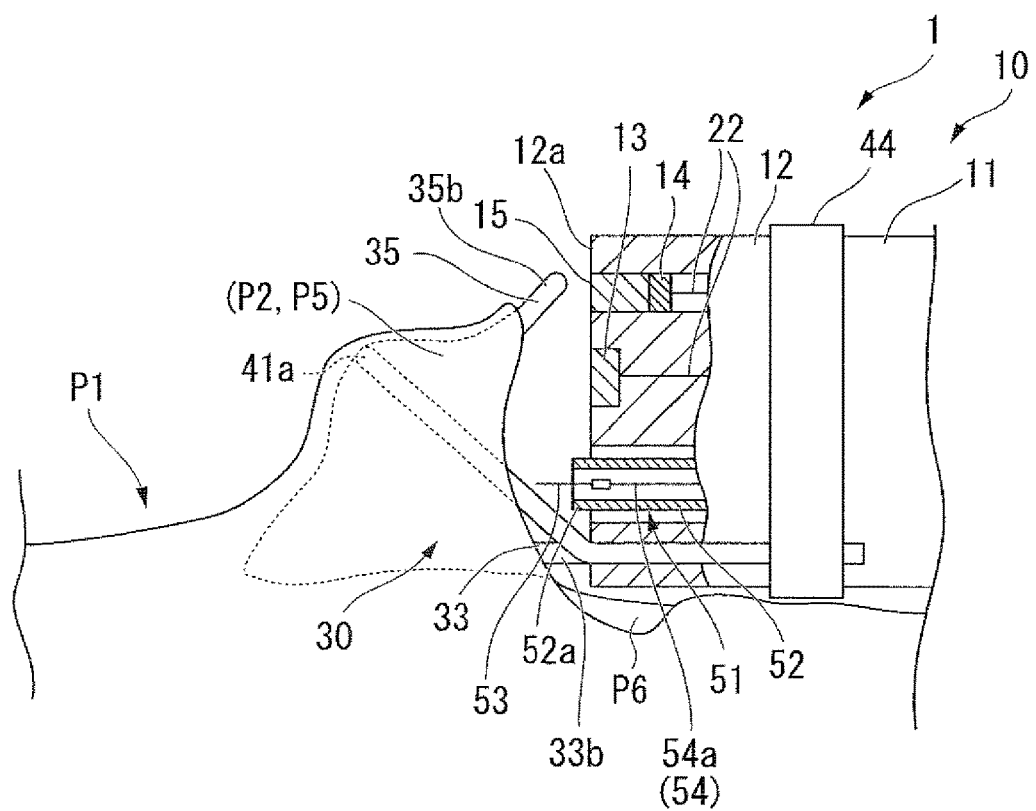
FIG. 13 is a side view showing a process of treatment in which the endoscope treatment system according to the embodiment of the present invention is adopted.

As necessary, the lifting instrument main body 31 may be caused to enter the space between the submucosal layer P5 and the muscle layer P6 such that the connecting portion 43 causing the first support portion 41 and the second support portion 42 to be connected with each other enter the space between the submucosal layer P5 and the muscle layer P6 (refer to FIG. 13). In this case, the submucosal layer P5 can be pushed up in a manner wider than that in a case where the submucosal layer P5 is pushed up with respect to the muscle layer P6 by the first lifting portion 35 and the second lifting portion 36.

After resection of the lesion mucous membrane site P1 ends, the operator removes the high-frequency knife 50 and the endoscope 10 from the gastrointestinal tract. Since the mucous membrane lifting instrument 30 for an endoscope is attached to the insertion portion 11 of the endoscope 10 through the attachment member 44, when the endoscope 10 is evulsed, the mucous membrane lifting instrument 30 for an endoscope is removed from the gastrointestinal tract together with the endoscope 10.

As described above, since the first lifting portion 35 and the second lifting portion 36 in the ESD treatment system 1 of the present embodiment cause the submucosal layer P5 to be spaced from the muscle layer P6, the operator of the ESD treatment system 1 can easily and visually recognize the site to be incised through the gap between the submucosal layer P5 and the muscle layer P6.

Moreover, in the present embodiment, since the first support portion 41 and the second support portion 42 press the submucosal layer P5 such that the submucosal layer P5 is tensioned between the first lifting portion 35 and the second lifting portion 36, the submucosal layer P5 can be prevented from drooping toward the muscle layer P6 side, and a favorable visual field can be obtained by using the observation unit 13 of the endoscope 10.

In addition, in a state where the first pressing portion 33 and the second pressing portion 34 are in contact with the muscle layer P6, the muscle layer P6 is held so as to be substantially flat. Therefore, the technique can be easily performed.

Modification Example

Figure 11:
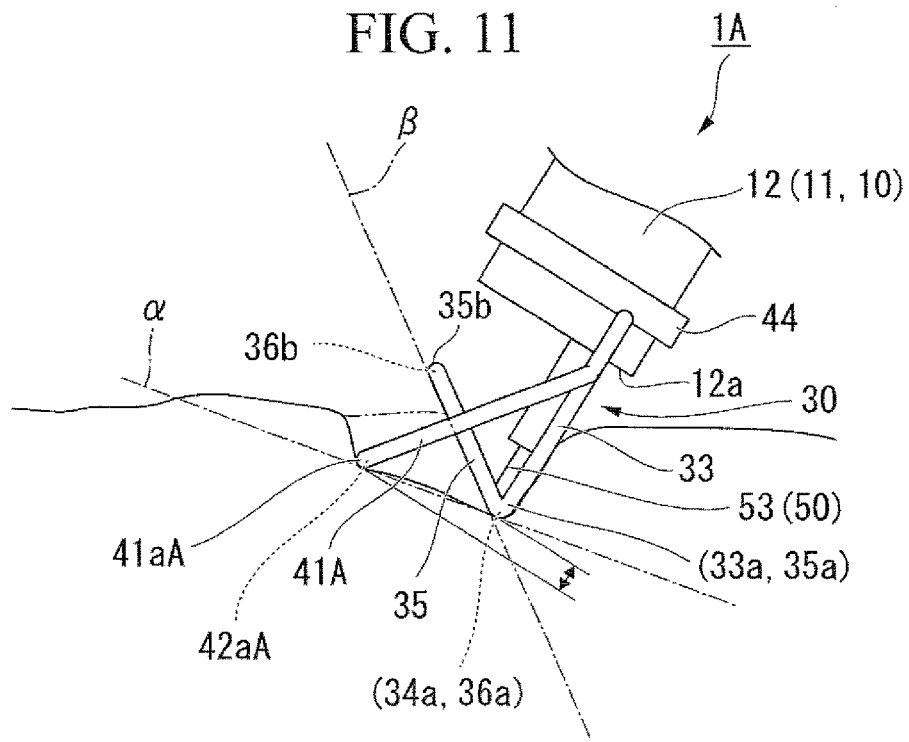
FIG. 11 is a side view showing a configuration and a using form of a modification example of the endoscope treatment system according to the embodiment of the present invention.
Figure 12:
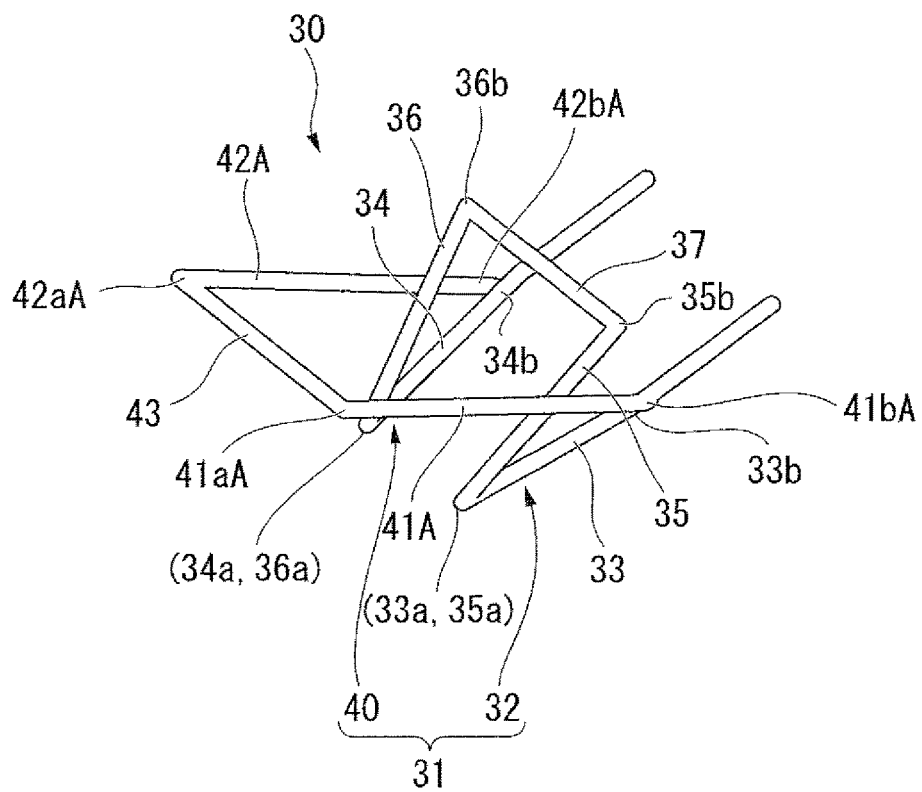
FIG. 12 is a perspective view showing the mucous membrane lifting instrument for an endoscope applied to the endoscope treatment system according to the modification example of the embodiment of the present invention.

Next, a modification example of the ESD treatment system 1 of the present embodiment will be described. FIG. 11 is a side view showing a configuration and a using form of the modification example of the ESD treatment system 1. FIG. 12 is a perspective view showing the mucous membrane lifting instrument for an endoscope applied to an ESD treatment system 1A of the present modification example.

As shown in FIGS. 11 and 12, the ESD treatment system 1A of the present modification example has a configuration different from that of the ESD treatment system 1 of the above-described embodiment in regard to the point that a first support portion 41A and a second support portion 42A respectively extending toward the distal end side farther than the distal end 41a of the first support portion 41 and the distal end 42a of the second support portion 42 are provided in place of the first support portion 41 and the second support portion 42.

A distal end 41aA of the first support portion 41A is positioned on the distal end side far from the distal end 33a of the first pressing portion 33 when viewed in a direction in which the first lifting portion 35 and the second lifting portion 36 overlap each other.

A distal end 42aA of the second support portion 42A is positioned on the distal end side far from the distal end 34a of the second pressing portion 34 when viewed in a direction in which the first lifting portion 35 and the second lifting portion 36 overlap each other.

In the present modification example, as shown in FIG. 11, a surface $\alpha$ is defined by the distal end 33a of the first pressing portion 33, the distal end 34a of the second pressing portion 34, the distal end 41aA of the first support portion 41A, and the distal end 42aA of the second support portion 42A. Since the distal end 41aA of the first support portion 41A and the distal end 42aA of the second support portion 42A are present in positions spaced from the rigid distal portion 12 from the distal end 33a of the first pressing portion 33 and the distal end 34a of the second pressing portion 34, the surface $\alpha$ is inclined with respect to the distal end surface 12a of the rigid distal portion 12.

In a case where the first support portion 41A, the second support portion 42A, and the connecting portion 43 are not provided, the outer surface of the mucous membrane is aligned along a surface $\beta$ which is defined by the first lifting portion 35 and the second lifting portion 36. In contrast, in the present modification example, since the outer surface of the mucous membrane is aligned along the surface $\alpha$ which is configured by the distal end 33a of the first pressing portion 33, the distal end 34a of the second pressing portion 34, the distal end 41aA of the first support portion 41A, and the distal end 42aA of the second support portion 42A, the incising electrode 53 of the high-frequency knife 50 can be brought into contact with the mucous membrane P2 at an obtuse angle.

In other words, when the high-frequency knife 50 is protruded from the treatment tool channel 19 in a state where the distal end 33a of the first pressing portion 33, the distal end 34a of the second pressing portion 34, the distal end 41aA of the first support portion 41A, and the distal end 42aA of the second support portion 42A are in contact with the inner wall of the gastrointestinal tract at the same time, the approaching angle of the incising electrode 53 with respect to the inner wall of the gastrointestinal tract becomes an obtuse angle.

In the present modification example, when the incising electrode 53 forms an obtuse angle with respect to the inner wall of the gastrointestinal tract, a risk of perforation of the gastrointestinal tract can be reduced.

In the present modification example, the first support portion 41A and the second support portion 42A are not necessarily fixed to the first pressing portion 33 and the second pressing portion 34. In other words, the ESD treatment system may include a ring-shaped cap which can be fixed to the outer peripheral portion of the distal end surface 12a of the rigid distal portion 12 of the endoscope 10, the first pressing portion 33 and the second pressing portion 34 fixed to the cap, and the first support portion 41A and the second support portion 42A which are fixed to positions different from the fixed positions of the first pressing portion 33 and the second pressing portion 34 in the cap.

Hereinbefore, the embodiment of the present invention has been described in detail with reference to the drawings. The specific configuration is not limited to the embodiment, and a design change and the like made without departing from the scope of the gist is also included in the present invention.

For example, the mucous membrane lifting instrument 30 for an endoscope according to the above-described embodiment does not have to include the connecting portion 37 causing the first lifting portion 35 and the second lifting portion 36 to be connected with each other, and the connecting portion 43 causing the first support portion 41 and the second support portion 42 to be connected with each other.

In addition, in the mucous membrane lifting instrument 30 for an endoscope according to the above-described embodiment, without providing the first pressing portion 33 and the second pressing portion 34, the proximal end 35b of the first lifting portion 35 and the proximal end 36b of the second lifting portion 36 may be attached to the rigid distal portion 12 of the endoscope. In this case, the first support portion 41 and the second support portion 42 are fixed to the proximal end 35b of the first lifting portion 35 and the proximal end 36b of the second lifting portion 36 or are fixed to the rigid distal portion 12 together with the first lifting portion 35 and the second lifting portion 36 via the ring-shaped cap described in the above-described modification example.

Hereinbefore, the embodiment of the present invention has been described with reference to the drawings. The specific configuration is not limited to the embodiment, and various changes made without departing from the scope of the spirit are also included in the present invention. The present invention is not limited to the foregoing description, and is limited to only the accompanying claims.

What is claimed is:

1. A mucous membrane lifting instrument for an endoscope, comprising:

a first support portion which has an outer circumference surface and a longitudinal axis extending distally from a distal end portion of an endoscope;

a second support portion which is provided at a position spaced from the outer circumference surface of the first support portion, and has an outer circumference surface and a longitudinal axis extending distally from the distal end portion of the endoscope;

a pressing portion which has a proximal end supported by the distal end portion of the endoscope, and has a distal end connected to the proximal end thereof and positioned more distally than the distal end portion of the endoscope, wherein the pressing portion includes:

a first pressing portion which has an outer circumference surface and is extended distally from the distal end portion of the endoscope, and a second pressing portion which is disposed at a position spaced from the outer circumference surface of the first pressing portion, has an outer circumference surface, and is extended distally from the distal end portion of the endoscope;

a lifting portion which is connected to the distal end of the pressing portion, extended from the distal end of the pressing portion towards a space between the first support portion and the second support portion, and passes through the space between the first support portion and the second support portion while having a gap with respect to each of the first support portion and the second support portion; and an attachment member configured to attach both of the first pressing portion and the second pressing portion to the endoscope, wherein the lifting portion includes:
- a first lifting portion which has an outer circumference surface and is connected to a distal end of the first pressing portion, and
- a second lifting portion which is disposed at a position spaced from the outer circumference surface of the first lifting portion, has an outer circumference surface, and is connected to a distal end portion of the second pressing portion.

2. The mucous membrane lifting instrument for an endoscope according to claim 1,
wherein the first support portion is formed to extend from the distal end portion of the endoscope while being inclined with respect to the first lifting portion, and
wherein the second support portion is formed to extend from the distal end portion of the endoscope while being inclined with respect to the first lifting portion.

3. The mucous membrane lifting instrument for an endoscope according to claim 1, further comprising:
a connecting portion which is provided to connect a proximal end of the first lifting portion and a proximal end of the second lifting portion.

4. The mucous membrane lifting instrument for an endoscope according to claim 1,
wherein each of the first lifting portion, the second lifting portion, the first support portion, and the second support portion has a rod shape.

5. The mucous membrane lifting instrument for an endoscope according to claim 1, further comprising:
a connecting portion which is provided to connect a distal end of the first support portion and a distal end of the second support portion.

6. An endoscope treatment system, comprising:
the mucous membrane lifting instrument for an endoscope according to claim 1; and
an endoscope to which the mucous membrane lifting instrument for an endoscope is attached.

* * * * *